(12) United States Patent
Ariza

(10) Patent No.: US 9,615,898 B2
(45) Date of Patent: Apr. 11, 2017

(54) TUBE FOR ORTHODONTICS

(76) Inventor: Joaquin T. Ariza, Bogota D.C. (CO)

( * ) Notice: Subject to any disclaimer, the term of this patent is extended or adjusted under 35 U.S.C. 154(b) by 135 days.

(21) Appl. No.: 14/386,931

(22) PCT Filed: Mar. 23, 2012

(86) PCT No.: PCT/IB2012/051412
§ 371 (c)(1),
(2), (4) Date: Jan. 16, 2015

(87) PCT Pub. No.: WO2013/140205
PCT Pub. Date: Sep. 26, 2013

(65) Prior Publication Data
US 2015/0125803 A1    May 7, 2015

(51) Int. Cl.
*A61C 7/28* (2006.01)
*A61C 7/14* (2006.01)

(52) U.S. Cl.
CPC ............... *A61C 7/282* (2013.01); *A61C 7/14* (2013.01); *A61C 7/141* (2013.01)

(58) Field of Classification Search
CPC ........... A61C 7/14; A61C 7/141; A61C 7/143; A61C 7/145; A61C 7/148; A61C 7/28; A61C 7/282; A61C 7/16
USPC ........................ 433/8, 9, 10, 13, 16, 17, 20
See application file for complete search history.

(56) References Cited

U.S. PATENT DOCUMENTS

| | | | | |
|---|---|---|---|---|
| 3,639,986 A | * | 2/1972 | Kesling | A61C 7/282 433/17 |
| 3,916,526 A | * | 11/1975 | Schudy | A61C 7/30 433/17 |
| 4,927,362 A | * | 5/1990 | Snead | A61C 7/282 433/17 |
| 4,936,774 A | * | 6/1990 | Stoller | A61C 7/12 433/110 |

(Continued)

FOREIGN PATENT DOCUMENTS

EP    0940125 A2    9/1999

OTHER PUBLICATIONS

International Search Report issued on Nov. 26, 2012 in International Application No. PCT/IB2012/051412.

*Primary Examiner* — Nicholas Lucchesi
(74) *Attorney, Agent, or Firm* — Pillsbury Winthrop Shaw Pittman LLP

(57) ABSTRACT

The invention provides a tube to be used in orthodontics wherein said tube replaces the use of brackets in an orthodontic treatment. The orthodontic tube of the present invention is surrounded by a resin and this resin also serves as a bond agent to affix the tube to a patient's tooth. The orthodontic tube serves as a conduit for an archwire in order to impose upon each tooth only the force required to reset the position of the tooth to a desired configuration relative to the other teeth in the patient's mouth.

The orthodontic tube of the present invention has an enhanced external shape that better adapts to the teeth's geometry and therefore, it offers enlarged area of contact (Continued)

between the flat outer section of the orthodontics tube and the tooth; in addition, this flat outer section lessens the volume of the tube that extends outwardly from the patient's teeth and the configuration of the internal space of the tube enhances the control of the archwire within the tube and diminishes the friction, all these characteristics facilitate the reposition the teeth.

14 Claims, 6 Drawing Sheets

(56) References Cited

U.S. PATENT DOCUMENTS

| | | | | |
|---|---|---|---|---|
| 5,197,873 | A | * | 3/1993 | Wong .................. A61C 7/16 433/9 |
| 5,356,288 | A | | 10/1994 | Cohen |
| 5,380,197 | A | * | 1/1995 | Hanson .................. A61C 7/303 433/18 |
| 5,540,586 | A | * | 7/1996 | Hanson .................. A61C 7/303 433/11 |
| 5,931,667 | A | | 8/1999 | Papandreas |
| 7,927,097 | B2 | * | 4/2011 | Cervera Sabater ...... A61C 7/16 433/9 |
| 2011/0053108 | A1 | | 3/2011 | Ariza |

* cited by examiner

TUBE FOR ORTHODONTICS

FIELD OF THE INVENTION

This invention relates to a tube with certain design characteristics to be used in orthodontics to align teeth and their position with regard to a person's bite. More particularly, the invention refers to an orthodontics tube which applies an individual magnitude of force to each tooth in a patient's mouth in order to correct malocclusions or crooked teeth and various other position flaws, whether cosmetic or structural.

BACKGROUND OF THE INVENTION

Orthodontic treatment is usually recommended for patients having teeth that are improperly positioned. In conventional orthodontic treatment, teeth move through the use of braces which are generally formed by bracket assemblies and an archwire. An orthodontist affixes each bracket assembly to the patient's teeth and engages the archwire through the slot of each bracket in order to apply force to the teeth toward their desired positions with the adjustment of the archwire in the course of the treatment.

Attempts have been made to provide a controlled force on each tooth as can be seen in PCT patent application PCT/US2007/067259 which shows an orthodontic brace comprising a set of brackets, including lateral anterior brackets, a cuspid bracket and a first bicuspid bracket, each bracket having a slot for receiving an archwire which provides help to move patient's teeth to an optimal position.

However, orthodontic treatments using braces have shown a number of drawbacks related with uncomfortable feelings of patients, increase of mouth illnesses and aesthetic problems. Patients under orthodontic treatments may develop particular gestures due to the unpleasant feeling of the brackets in the mouth due to the fact that the brackets extend outwardly and the patients are not used to these appliances on their teeth.

In addition, these brackets may cause blisters in the oral cavity and could increase dental plaque, which could lead to dental cavities or periodontal problems such as gingivitis.

In addition, patients also report various aesthetic problems since braces usually are visible and therefore, these orthodontic treatments dramatically change the appearance of a patient.

To improve the cosmetic appearance of the brackets, ceramic injection molded brackets have been developed as shown in U.S. Patent 2010/173256 by Ormco Corporation. In addition, U.S. Pat. No. 7,252,506 issued to 3M Innovative Properties Company has also offered a solution to the aesthetic problems of the braces by means of using an arch member made of a stain-resistant transparent or translucent polymer having aesthetic characteristics in the orthodontic treatment.

In order to reduce the volume of the braces in the mouth and to decrease the aesthetic problems derived from the use of brackets, alternative orthodontic systems have been developed as shown in U.S. patent application Ser. Nos. 12/548,407 and 13/035,871 by Ariza, Joaquin. These inventions relate to an orthodontic system for teeth alignment without brackets and they describe an orthodontic system using a tube, instead of brackets, and a resin that goes over the tube and affixes the tube to a patient's tooth hereby constructing a point to apply force through an archwire.

In addition, tubes (1) like the one depicted in FIG. 2 of the present invention have been used in orthodontic systems to align teeth (3) in conjunction with a wire (4) that goes through the tubes (1).

However, in spite of the efforts mentioned in the field of orthodontics, there is still a need for obtaining an improved orthodontics tube with an enhanced external shape that better adapts to the teeth's geometry in order to obtain larger adherence area and consequently, to reposition the teeth more efficiently.

In view of the aforementioned, it would be desirable to develop methods for providing orthodontic treatments having no side effects for the patients.

The present invention provides an orthodontics tube to be used in orthodontic treatments wherein the reported drawbacks of the current orthodontic methods are overcome.

SUMMARY OF THE INVENTION

The present invention relates to a tube for orthodontics wherein said orthodontics tube has an internal space and openings at both ends, the orthodontics tube has a flat outer section simulating the shape of the letter "D", with the same shape in its internal space and both ends have beveled inside edges. This special configuration of the orthodontics tube better adapts to the teeth's geometry and therefore, it offers enlarged area of contact between the flat outer section of the orthodontics tube and the tooth; in addition, this flat outer section lessens the volume of the tube that extends outwardly from the patient's teeth and the configuration of the internal space of the tube enhances the control the archwire within the tube and diminishes the friction, all these characteristics facilitate the repositioning of the teeth.

The orthodontics tube of the present invention is surrounded by a resin and this resin also serves as a bond agent to affix the orthodontics tube to a patient's tooth. The orthodontics tube serves as a conduit for an archwire in order to impose upon each tooth only the required force to reset the tooth's position.

These and other features of the invention are described in more detail in the paragraphs that follow and are illustrated in the accompanying drawings.

DETAILED DESCRIPTION OF THE INVENTION

The current orthodontic systems use the combination of a bracket and an archwire to reposition teeth in a patient's mouth.

The present invention provides a tube for orthodontics wherein said tube replaces the use of brackets in an orthodontic treatment. The orthodontic tube of the present invention is surrounded by a resin and this resin also serves as a bond agent to affix the orthodontic tube to a patient's tooth. The orthodontic tube serves as a conduit for an archwire in order to impose upon each tooth only the required force to reset the position of the tooth to a desired configuration relative to the other teeth in the patient's mouth.

The orthodontic tube of the present invention has an enhanced shape that offers enlarged area of contact between the flat outer section of the orthodontic tube and the tooth and this flat outer section lessens the volume of the orthodontic tube that extends outwardly from the patient's teeth and the configuration of the internal space of the orthodontic tube enhances the control the archwire within the orthodontic tube and diminishes the friction between them.

Figure 1:
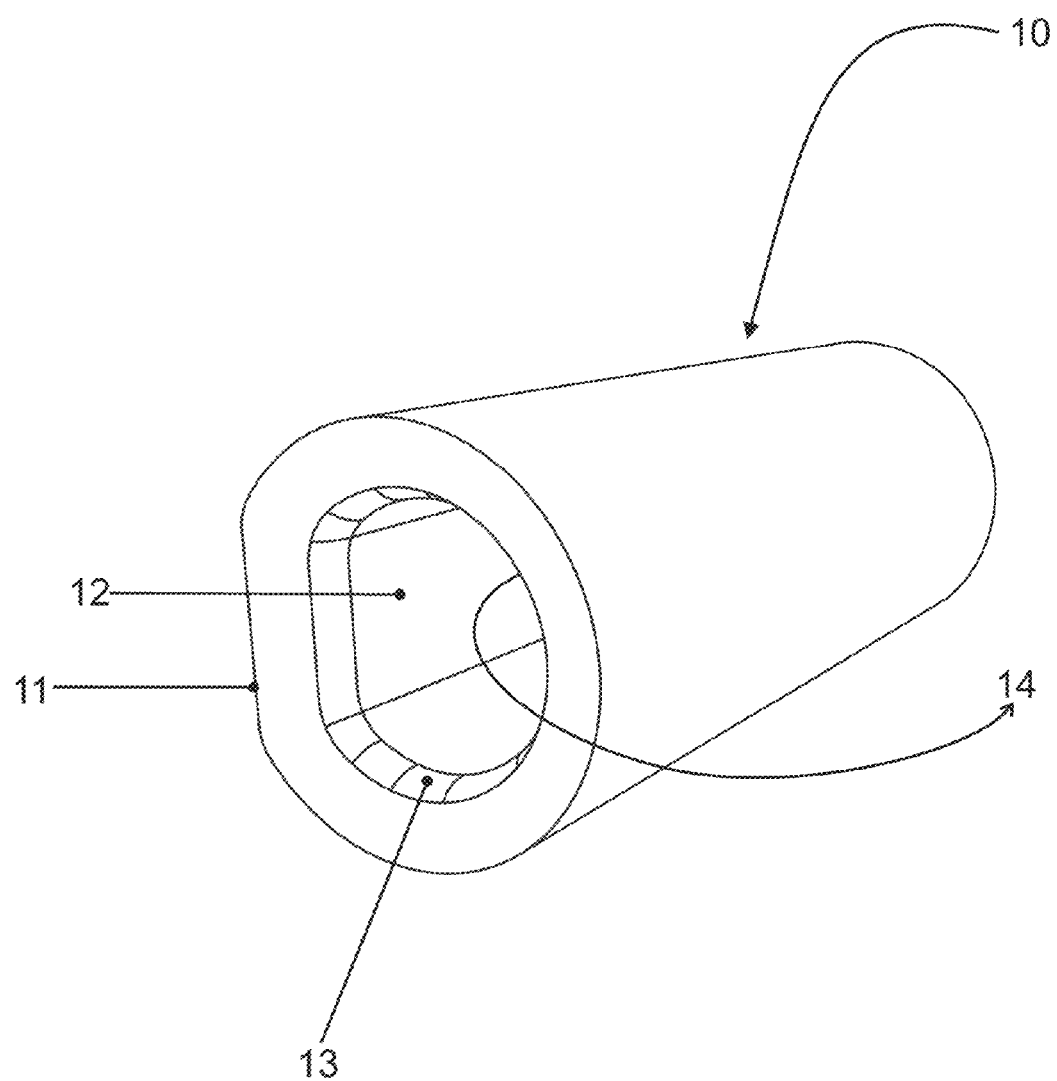
FIG. 1 is a perspective view of an orthodontics tube in accordance with one embodiment of the invention.

An exemplary orthodontic tube (10) according to one embodiment of the present invention is depicted in FIG. 1. The orthodontic tube (10) is a hollow device with an internal space (14) and openings at both ends. The orthodontic tube (10) has a flat outer section (11) simulating the shape of the letter "D", with the same shape in its internal space (14) and both ends have beveled inside edges (13).

The flat outer section (11) of the orthodontic tube (10) is intended to face the tooth (30) when adhered to it by means of a bond agent. Due to the special shape of this flat outer section (11) a larger area of contact is obtained, which contributes to an improved fixation of the orthodontic tube (10) to a patient's tooth (30).

There are different types of bond agents that can be used for the purposes of adhering the orthodontic tube (10) to a patient's tooth (30); however, a preferred bond agent is a resin (20) which includes any kind of resin used in dentistry and/or other substitute appropriate materials that allow manipulation on teeth e.g., ceramics, polymeric materials, etc. The resin and/or substitute material is of the same color as the teeth being treated. However, the term resin also includes a resin or substituted material of any color if chosen by the patient.

In another embodiment of the invention, the flat outer section (11) of the external configuration of the orthodontic tube (10) can be corrugated or can have grooves (not depicted in the figures) to offer more adherence to a patient's tooth (30).

Figure 2:
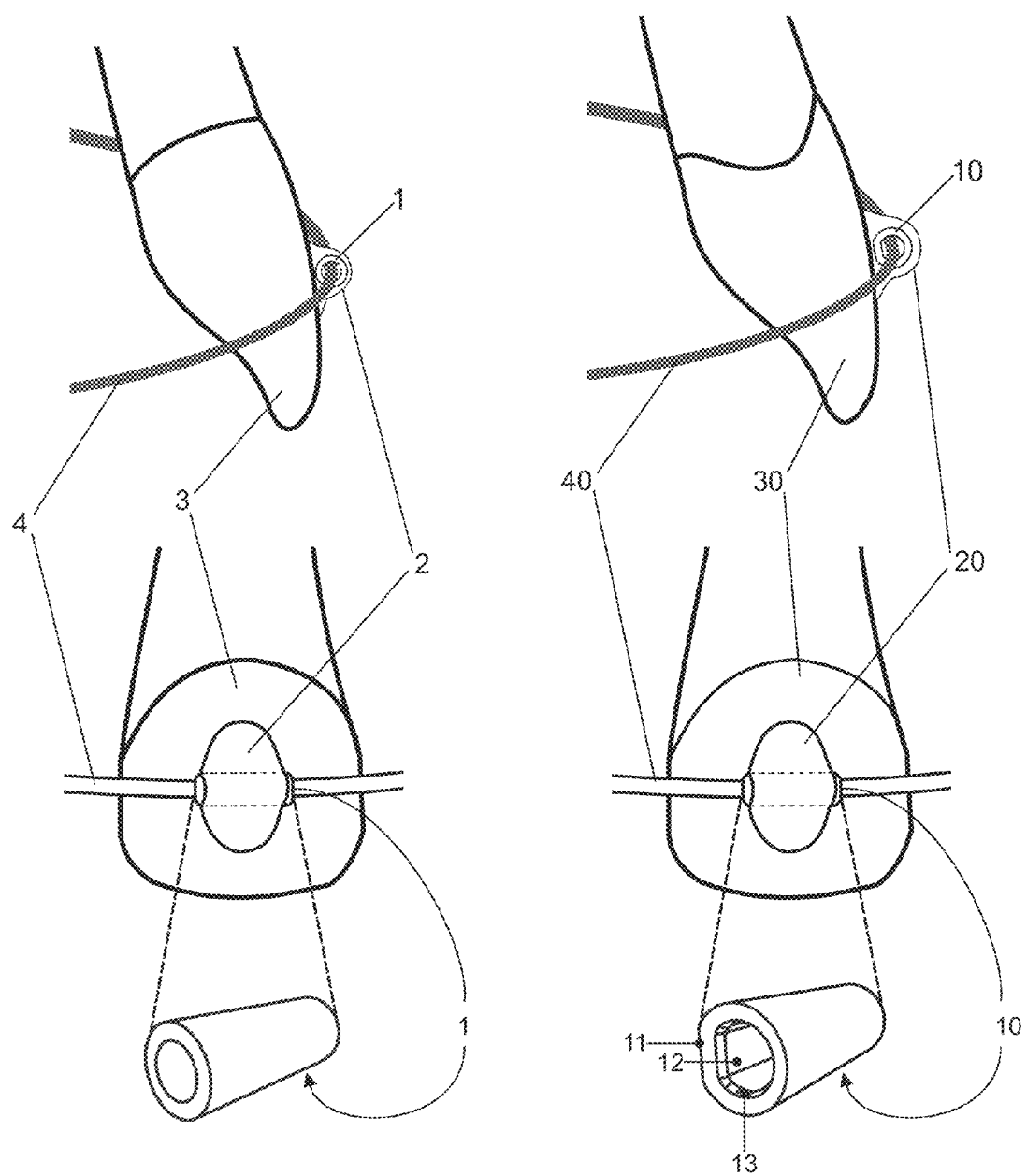
FIG. 2 is a comparative of the tube currently used in orthodontics and the orthodontics tube of the present invention.

With reference to FIG. 2, one can compare the structural differences between the orthodontic tube (10) of the present invention and the tube (1) of the state of the art. The tube (1) of the state of the art is cylindrical and therefore, the contact area between the tube (1) and the tooth (3) is much lesser than the contact area obtained with the new shape of the letter "D" that is reproduced by the orthodontic tube (10) of the present invention. In addition, since the orthodontic tube (10) has a flat outer section (11), this feature lessens the volume of the orthodontic tube (10) that extends outwardly from the patient's teeth (30) and consequently, the uncomfortable feeling of the brackets of the state of the art are reduced by the use of the orthodontic tube (10) of the present invention.

In addition, due to the internal configuration of the orthodontic tube (10), which exhibits a flat inner section (12), the archwire (40) that goes through the orthodontic tube (10) would have an enhanced control that would allow the orthodontist to apply different stresses and forces to reposition the teeth. The tube (1) of the state of art does not offer this superior control of the archwire (4), since its inner space is cylindrical and therefore, limits the possibility of performing different movements to the archwire (4).

With the configuration of the improved orthodontic tube (10) of the present invention is possible to perform different types of tooth movements; for example: a) torque movements described as the rotation of a tooth on the long axis moving the root of the tooth in a buccal, lingual or labial direction; b) tipping movements, where the root of the tooth is tipped labially (lip) or lingually (tongue) to correct the angle of the crown of the tooth; and c) rotational movement, where the tooth is moved in a rotational direction about its longitudinal axis.

As depicted in FIGS. 1 and 2, the orthodontic tube (10) has ends with beveled inside edges (13) that allow better slip of the archwire (40) inside the orthodontic tube (10) and consequently, reducing the friction between them.

Figure 3:
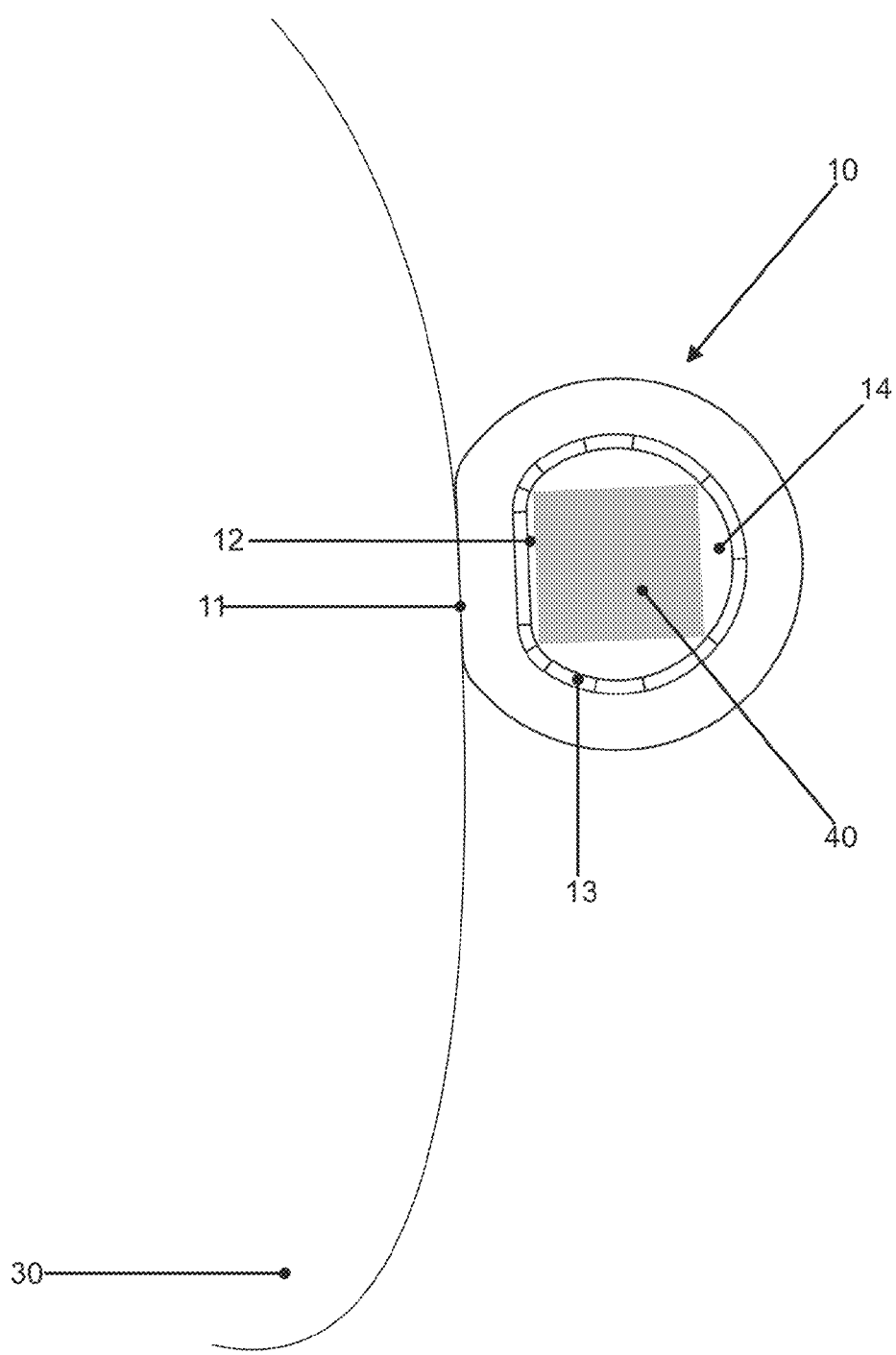
FIG. 3 is a cross-section view of an archwire inserted in the orthodontics tube in accordance with one embodiment of the invention.

In the embodiment illustrated in FIG. 3, the archwire (40) has a rectangular shape, and it is positioned through the orthodontic tube (10) along the occlusal plane of the teeth.

Orthodontic archwires are available in various forms and sizes. Particularly, archwires are cylindrical or rectangular in its cross-sectional area. The rectangular arch wires can have cross-sections of 0.010 inches (0.254 mm), 0.012 inches (0.3048 mm), 0.013 inches (0.3302 mm), 0.014 inches (0.3556 mm), 0.016 inches (0.4064 mm), etc.

As can be seen in FIG. 3, the orthodontic tube (10) has a special design with flat inner section (12) that prevents the rotation of a rectangular archwire (40) within the orthodontic tube (10).

Figure 4:
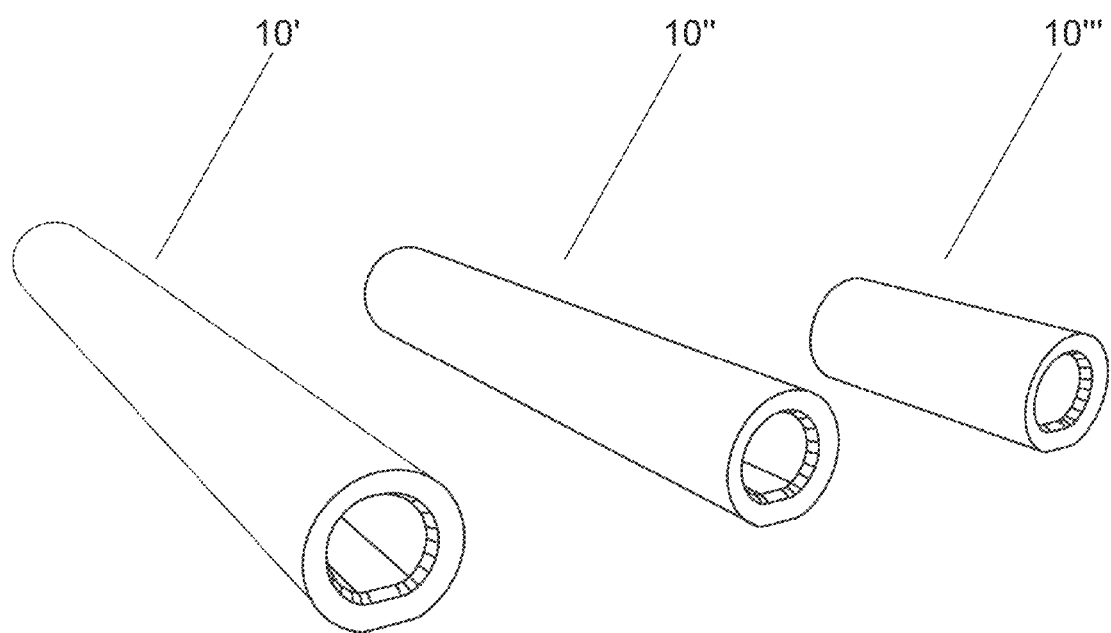
FIG. 4 is a perspective view of orthodontics tubes with different lengths in accordance with various embodiments of the invention.

With reference to FIG. 4, orthodontic tubes (10) with different lengths are encompassed by the present specification. The orthodontic tube (10) can have different lengths depending on the size of the tooth and the type of correction required; in particular, the orthodontic tube can be 5 mm (10'), 3 mm (10'') and 2 mm (10''') in length.

The orthodontic tube (10) is preferably metallic; however the orthodontic tube can be made of any appropriate hard material such as carbon, polymeric compounds, hard plastics, etc.

The orthodontic tube (10) is surrounded and adhered to a tooth by means of a resin (20) at the moment that it is fixed in a patient (see FIG. 2).

Figure 6:
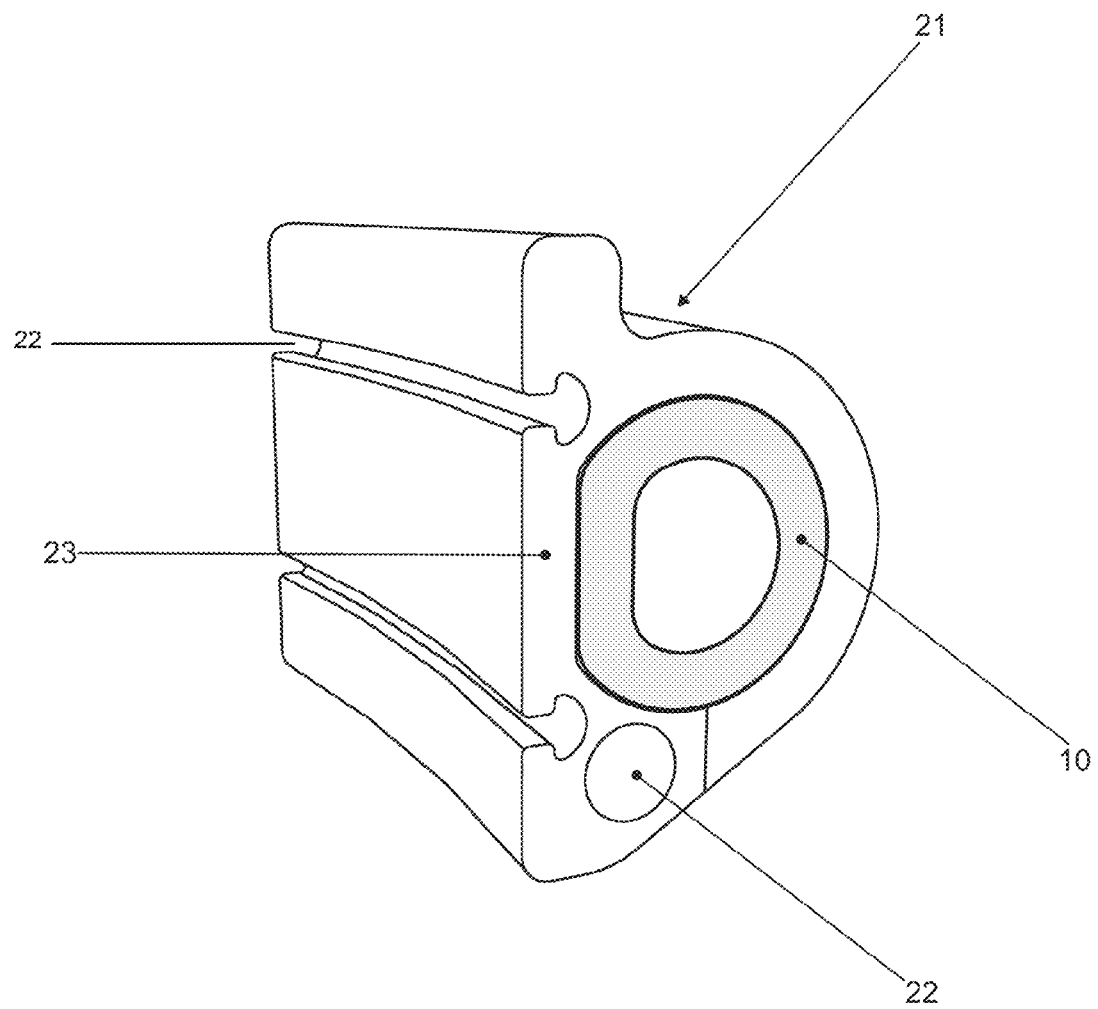
FIG. 6 shows an orthodontics tube in accordance with one embodiment of the invention which has been preassembled in one single piece with a resin.

However, in another embodiment of the invention, it is possible to obtain a preassembled orthodontic tube (10) with a resin (20) and therefore, the orthodontist can obtain this preassembled orthodontic tube which only needs to be adhered to the tooth with a very small amount of resin (20). In the embodiment illustrated in FIG. 6, the surrounded resin of the orthodontic tube is preassembled in one single piece (21) to be adhered to the tooth in one single step by the orthodontist when performing the treatment in a patient. This embodiment facilitates the work of the orthodontist and assures that only the necessary quantity of resin (20) will surround the orthodontic tube (10) guaranteeing that orthodontic system using the orthodontic tube (10) of the invention will have very low volume and therefore, they will not project from the patient's teeth as in the case of brackets that have a very bulky projection causing discomfort to the patient.

Another option; the orthodontic tube (10) may have an opening (22) in the preassembled resin (21) to introduce other accessories to conform to the orthodontics system. In addition, the preassembled resin (21) that surrounds the orthodontic tube (10) can have grooves (24) to offer greater adhesion to the tooth and a mechanical lock to the orthodontic system. This preassembled resin (21) has a base (23)

to be adhered to a tooth (30) and its thickness may vary depending on the volume of each tooth.

Figure 5:
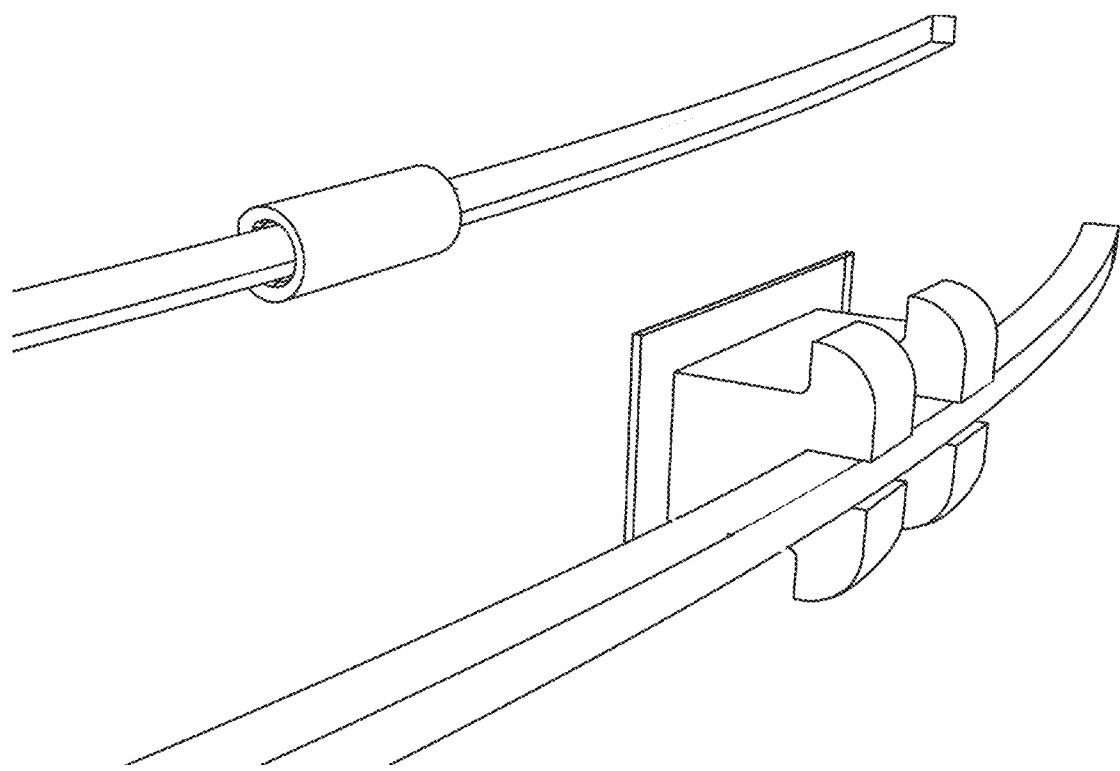
FIG. 5 illustrates an archwire with an orthodontics tube, in accordance with one embodiment of the invention, compared with braces of the state of the art.

The orthodontic treatment with the orthodontic tubes (10) of the invention will significantly reduce the undesirable side effects that have been reported with the use of brackets. This advantage is a consequence of the fact that the projection profile of the orthodontic tubes (10) is much smaller than that of the brackets as can be seen in FIG. 5 that shows a real scale comparison between the orthodontic tube (10) of the invention and a bracket of the state of the art.

As the treatment is carried out, the orthodontist could modify the position of the orthodontic tube (10) in order to guide the movement of the teeth or could vary the position of the archwire (40) within the inner space (14) depending on the requirements of the treatment for the patient.

Additionally, it is also clear that the orthodontic tube (10) of the present invention can be adapted to cover any number of teeth in the maxilla or in the mandible.

Many other changes and modifications of the present invention may be made, as desired, by those skilled in the art without departing from the scope of the invention.

The invention claimed is:

1. An orthodontic tube, comprising:
    an internal space with openings at both ends;
    a flat outer section such that the orthodontic tube has a cross section with an outer shape of the letter "D"; and
    a flat inner section that is parallel to the flat outer section such that the cross section of the tube has an inner shape of the letter "D", wherein
    the flat outer section of the orthodontic tube is corrugated and has grooves, and
    both ends of the orthodontic tube have beveled inside edges.

2. The orthodontic tube of claim 1, wherein the flat outer section is to face a tooth when adhered to the tooth and this flat outer section offers a larger area of contact between the flat outer section of the orthodontic tube and the tooth than an area of contact for a curved outer section.

3. The orthodontic tube of claim 1, wherein the flat outer section lessens the volume of the orthodontic tube that extends outwardly from the patient's teeth.

4. The orthodontic tube of claim 1, wherein the flat inner section offers better control of a rectangular archwire and prevents a rotation of the rectangular archwire within the orthodontic tube.

5. The orthodontic tube of claim 1, wherein the beveled inside edges allow better slip of the archwire inside the orthodontic tube, reducing the friction between the archwire and the beveled inside edges.

6. The orthodontic tube of claim 1, wherein the length of the orthodontic tube could be 5 mm, 3 mm or 2 mm.

7. The orthodontic tube of claim 1, is made of metallic or any appropriate hard material such as carbon, polymeric compounds or hard plastics.

8. The orthodontic tube of claim 1, wherein the orthodontic tube is surrounded by a piece of resin and adhered to a tooth at the moment that it is fixed in a patient.

9. The orthodontic tube of claim 8, wherein the piece of resin is preassembled in one single piece to be adhered to the tooth in one single step.

10. The orthodontic tube of claim 9, wherein the preassembled resin has an additional opening in the same direction of the tube to introduce other accessories to conform to an orthodontics system.

11. The orthodontic tube of claim 9, wherein the preassembled resin that surrounds the orthodontic tube has grooves to offer greater adhesion to the tooth and a mechanical lock to an orthodontic system.

12. The orthodontic tube of claim 9, wherein the preassembled resin has a base to be adhered to a tooth and its thickness may vary depending on the volume of a tooth to which it is adhered.

13. A system for orthodontics to be applied on a plurality of teeth, comprising:
    a plurality of tubes each of which has an internal space with openings at both ends of the tube, wherein each tube has a flat inner section such that a cross section of the tube has an inner shape of the letter "D"; and
    a wire passing through the plurality of tubes, wherein the wire has a cross section with a rectangular shape, wherein the inner "D" shape of each tube reduces friction, between the wire and the tube, which limits turn or rotation of the rectangular wire inside the tube, and wherein a force of torsion applied to the wire produces forces and inclinations in a direction along the vestibular palatine of the plurality of teeth to change their positions.

14. The system of claim 13, wherein:
    each tube has a flat outer section that is parallel to the flat inner section of the tube such that the cross section of the tube has an outer shape of the letter "D";
    the flat outer section is corrugated and has grooves and is to face a corresponding tooth in the plurality of teeth when adhered to the tooth to provide a larger area of contact between the flat outer section and the corresponding tooth than an area of contact for a curved outer section; and
    each tube is surrounded by a piece of resin to be adhered to the corresponding tooth, wherein the piece of resin cures into the grooves of the tube to enhance adhesion to the tooth.

* * * * *